Dec. 23 , 1952 L. L. BROOKS Plant Pat. 1,159

AZALEA PLANT

Filed Jan. 7, 1952

WITNESS

Addison E. Avery

INVENTOR

LENARD L. BROOKS

BY Webster & Webster

ATTYS.

Patented Dec. 23, 1952

Plant Pat. 1,159

UNITED STATES PATENT OFFICE 1,159

AZALEA PLANT

Lenard L. Brooks, Modesto, Calif.

Application January 7, 1952, Serial No. 265,224

1 Claim. (Cl. 47—60)

This invention is directed to a new and distinct variety of azalea plant, such plant being principally characterized by its ease of reproduction on its own roots; its excellence as a greenhouse forcing and garden variety; its rapid yet much branched compact habit of growth; its large leaves, heavy-textured when mature; and its large ruffled hose in hose red flowers with an undertone of orange.

The variety is a cross produced in the experimental garden of my nursery at Modesto, California; the cross having been made by pollen from the Kurume azalea Hexe used on the Belgian Indica azalea Wm. Van Orange. Neither of the parent varieties are patented.

The cross as produced above was clearly novel and evidenced high possibilities for commercial use. It was therefore taken for propagation by cuttings, and the first cuttings produced azalea plants which carried forward all of the distinguishing features of the parent.

The original asexual propagation of the variety by cuttings was carried out in my experimental garden located as aforesaid. Subsequent propagations of the variety by cuttings further evidences that the variety is fixed in its floricultural characteristics.

In the drawings:

Fig. 2 is a somewhat diagrammatic perspective illustration of one of the flowers with the trumpets separated.

Figure 1:
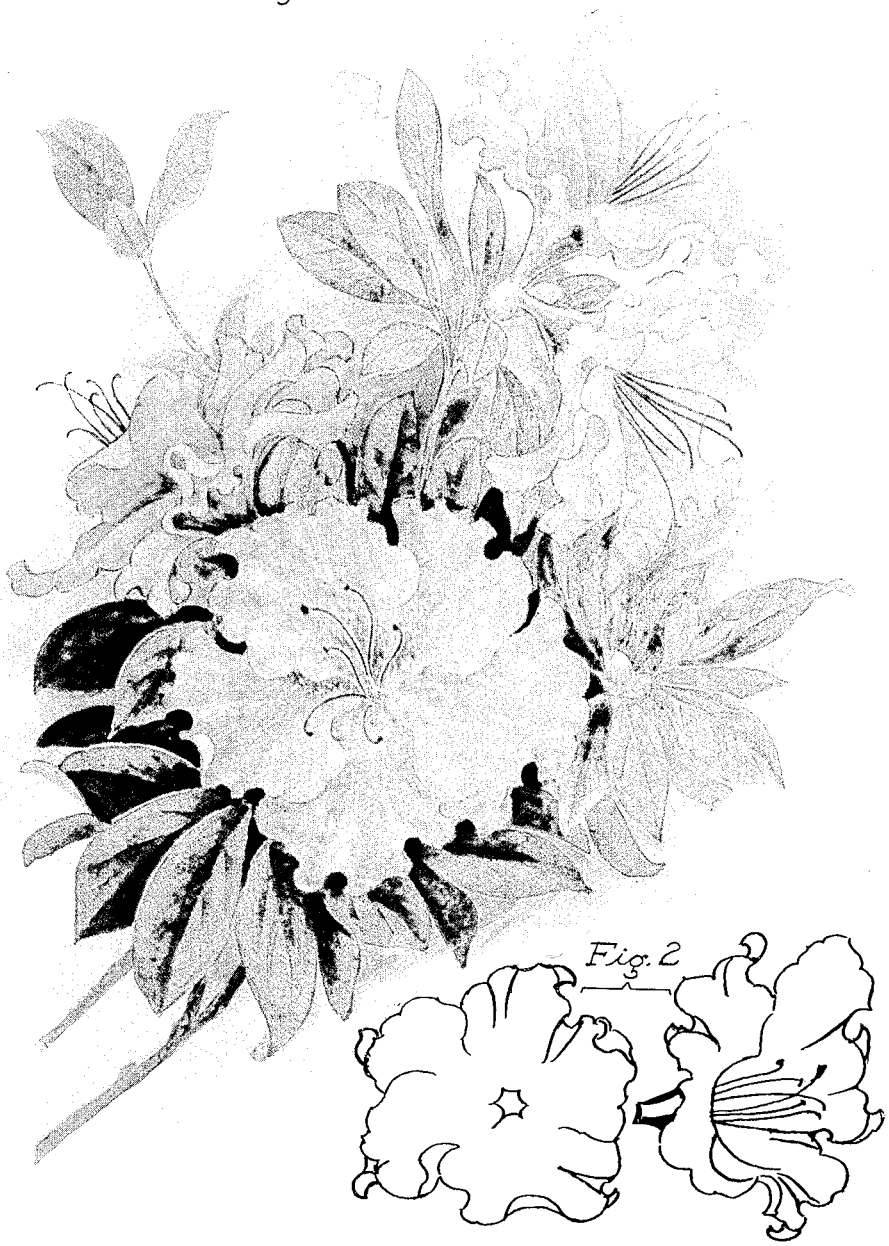
Fig. 1 is a perspective view of twigs, with leaves and flowers; such leaves and flowers being of the color when the plant is grown outdoors.

Referring now more specifically to the botanical details of this new and distinct variety of azalea plant, the following is an outline description thereof; all major color plate identifications being by reference to Maerz and Paul Dictionary of Color.

*Plant*

Form: Many branched, rounded, symmetrical. In the young plants the height and breadth are about equal, but as they attain age, the breadth gradually becomes greater than the height.

Growing habit: Dense and bushy with heavy mature foliage. The rate of growth is very rapid, often attaining a spread of three feet in four years from the rooted cuttings. A minimum of pruning is required to produce shapely plants.

Blooming habit: It blooms out evenly over the entire plant both when forced in the greenhouse or flowered naturally in the garden. From two to six flowers are produced on each stem.

Blooming season: March-April in central California, although it is easily forced out of season in the greenhouse.

Foliage:

*Size.*—Mature leaves average 1¼″ to 2½″ in length.

*Color.*—On outdoor grown plants: New leaves, light yellow green (20–L–7); mature leaves, medium dark green (24–L–1); under side lighter green. On greenhouse grown plants: The color of the mature leaves becomes a much deeper green, deepening in some cases to jungle green (32–L–12), but with the under side remaining somewhat lighter (31–A–9).

*Shape.*—Oval, pointed.

*Aspect.*—Glossy but not smooth.

*Texture.*—Heavy.

*Edge.*—Smooth.

*Ribs and veins.*—Normal.

Stems of foliage: *Color.*—Light brown (14–C–10).

Flower:

*Size.*—Large, averaging 2½″ to 3½″ in diameter.

*Borne.*—Clusters of two to six flowers held high above the foliage, with no drooping effect.

*Stem.*—Medium length, strong.

*Form.*—Hose in hose with petals heavily ruffled, giving flowers a very pleasing and distinctive appearance. The outer hose or trumpet rarely develops fully when flowered naturally in the garden. The outer hose nearly always develops fully when forced in the greenhouse.

*Permanence.*—Long lasting with no fading or changing color as the flowers age.

*Petalage.*—Five petals on each hose or flower.

*Color.*—On outdoor grown plants: Red with an undertone of orange, producing a rose shade (1–J–4 through 1–J–6), with the outside of the outer trumpet sometimes showing tracings of white, and the upper part of the throat overlaid with maroon (4–L–6). On greenhouse grown plants: The flowers are a deeper shade (3–J–6), with the upper part of the throat overlaid with a deeper maroon (7–L–6).

Petals:

*Texture.*—Heavy.

*Appearance.*—Velvety, inside and out. Edges heavily ruffled.

*Size.*—Average, 1¼″ to 1½″ wide, and 1½″ to 1¾″ long.

*Shape.*—Ovate, narrowing abruptly at lower end.

*Arrangement.*—Normal Kurume type.

*Persistence.*—Remains firm without wilting until flower is ready to fall.

Reproductive organs:

*Stamens.*—Five. About the same color as the petals.

*Pollen.*—White. Anthers about the same color as the petals.

*Style.*—About 1¼″ long. Both style and stigma well developed. The color is about the same as the petals.

*Ovaries.*—Normal.

As compared to other and well known varieties of azalea plants, the instant variety somewhat resembles the Kurume variety Hexe, the pollen parent, but with the following differences.

1. The flowers are larger.
2. The petals are very ruffled.
3. There is a substantial color distinction. While the flowers of the present variety are basically red they have an undertone of orange of about the shade found in the seed parent, Wm. Van Orange, instead of the blue undertone found in the pollen parent, Hexe. This orange undertone to the red gives the flower a brilliant, lively appearance, and it shows up particularly well under artificial light, while the blue undertone of Hexe tends to deaden the color under the same conditions.
4. The outside hose or trumpet nearly always develops fully when forced in the greenhouse.
5. The leaves are larger.

6. The plant branches better and makes a more uniform growth.

Tests indicate that the present variety of azalea plant has approximately the hardiness of the Hexe azalea plant and is better for greenhouse forcing or for garden culture.

As with the azalea Hexe, the present variety starts very easily from cuttings.

The plant and its flower herein described may vary in slight detail due to climatic and soil conditions under which the variety may be grown. For example, foliage color of an azalea is closely related to the conditions under which the plant is grown and the amount of acid used in its culture, and such color can thus vary substantially.

Having thus described the invention, I claim:

A new and distinct variety of azalea plant, of the Kurume class, comprised of a cross between the Kurume azalea Hexe and the Belgian Indica azalea Wm. Van Orange; characterized by its ease of reproduction on its own roots; its excellence as a greenhouse forcing and garden variety; its rapid and yet much branched, compact, uniform habit of growth; its large leaves—heavy textured when mature and deep green when greenhouse forced; and its large ruffled hose in hose red flowers having an undertone of orange which produces a rose shade.

LENARD L. BROOKS.

No references cited.